(12) United States Patent
Ozeki et al.

(10) Patent No.: US 8,877,918 B2
(45) Date of Patent: Nov. 4, 2014

(54) NUCLEIC ACID EXTRACTION METHOD

(75) Inventors: Yoshihiro Ozeki, Fuchu (JP); Akiyo Yamada, Fuchu (JP); Nobuhiro Sasaki, Fuchu (JP); Hitoshi Wake, Musashino (JP); Takeyuki Mogi, Musashino (JP); Tomoyuki Taguchi, Musashino (JP)

(73) Assignees: Tokyo University of Agriculture and Technology, Tokyo (JP); Yokogawa Electric Corporation, Tokyo (JP)

( * ) Notice: Subject to any disclaimer, the term of this patent is extended or adjusted under 35 U.S.C. 154(b) by 116 days.

(21) Appl. No.: 13/362,373

(22) Filed: Jan. 31, 2012

(65) Prior Publication Data
US 2012/0197008 A1     Aug. 2, 2012

(30) Foreign Application Priority Data

Jan. 31, 2011 (JP) ................. 2011-018172

(51) Int. Cl.
| | | |
|---|---|---|
| *C07H 21/00* | (2006.01) | |
| *C12N 15/10* | (2006.01) | |
| *C12N 1/06* | (2006.01) | |
| *C12Q 1/68* | (2006.01) | |

(52) U.S. Cl.
CPC .......... *C12Q 1/6806* (2013.01); *C12N 15/1003* (2013.01); *C12N 1/06* (2013.01)
USPC ...... 536/25.41; 536/25.4; 536/25.42

(58) Field of Classification Search
None
See application file for complete search history.

(56) References Cited

U.S. PATENT DOCUMENTS

| 4,830,969 A | 5/1989 | Holmes |
|---|---|---|
| 2008/0264842 A1 | 10/2008 | Hukari et al. |

FOREIGN PATENT DOCUMENTS

| EP | 0393744 A1 | 10/1990 |
|---|---|---|
| EP | 0696638 A1 | 2/1996 |
| EP | 0795602 A2 | 9/1997 |
| EP | 1944368 A1 | 7/2008 |
| JP | 02-292298 A | 12/1990 |
| JP | 7-2120 B2 | 1/1995 |
| JP | 2001-157584 A | 6/2001 |
| JP | 3866762 B2 | 1/2007 |
| JP | 2008-167722 A | 7/2008 |
| JP | 2009-254384 A | 11/2009 |
| JP | 2010-507071 A | 3/2010 |
| WO | 9636706 A1 | 11/1996 |
| WO | 2009025690 A2 | 2/2009 |

OTHER PUBLICATIONS

Simmon et al. Journal of Microbiological Methods (2004), vol. 56, pp. 143-149.*
Zhu et al. Nature Protocols (2006), vol. 1, pp. 3088-3093.*
Extended European Search report corresponding to European Patent Application No. 12153079.4, dated Apr. 3, 2012, English language translation.
David S. Holmes, et al., A Rapid Boiling Method for the Preparation of Bacterial Plasmids, Department of Biological Sciences and Center for Biological Macromolecules, New York, Analytical Biochemistry vol. 114, pp. 193-197 (1981), in English language.
A. Abolmaaty, et al., Effects of Lysing Methods and Their Variables on the Yield of *Escherichia coli* O157: H7 DNA and its PCR Amplification, Journal of Microbiological Methods vol. 34, pp. 133-141 (1998), in English language.

* cited by examiner

*Primary Examiner* — Patrick Lewis
(74) *Attorney, Agent, or Firm* — Sughrue Mion, PLLC

(57) ABSTRACT

There is provided a nucleic acid extraction method applicable to microbes in a relatively wide range, and capable of rapidly extracting nucleic acid. The nucleic acid extraction method comprises the steps of introducing a cell suspension into a vessel, sealing the vessel, and preheating a heater up to a set temperature not lower than 100° C. Further, the method comprises the step of bringing the vessel into contact with the heater heated up to the set temperature, thereby heating the cell suspension housed in the vessel up to a prescribed highest temperature at not lower than 100° C. with the vessel held in a sealed state.

13 Claims, 7 Drawing Sheets

FIG. 6

| SAMPLE | DETECTION VALUE (a.u.) |
|---|---|
| TREATMENT ACCORDING TO EMBODIMENT 4 (25°C) | 0.15 |
| TREATMENT ACCORDING TO EMBODIMENT 4 (95°C) | 0.25 |
| TREATMENT ACCORDING TO EMBODIMENT 4 (132°C) | 12.99 |
| STERILIZATION TREATMENT | 0.20 |
| AUTOCLAVE STERILIZATION TREATMENT | N.D. |

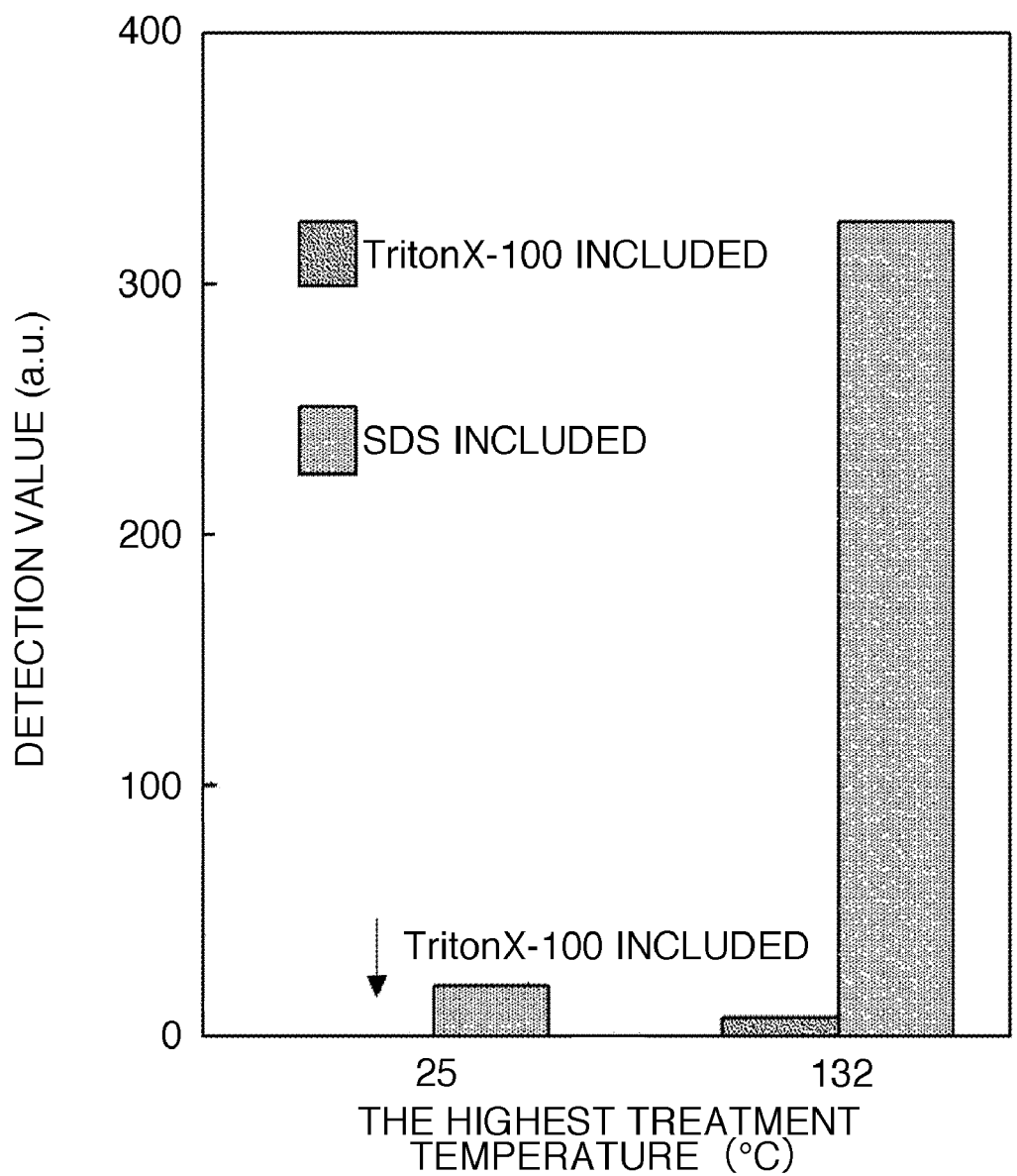

NUCLEIC ACID EXTRACTION METHOD

This application claims priority from Japanese Patent Application No. 2011-018172, filed on Jan. 31, 2011, the entire contents of which are herein incorporated by reference.

BACKGROUND

1. Technical Field

The present invention relates to a nucleic acid extraction method for extracting nucleic acid from a cell.

2. Related Art

In order to extract nucleic acid, it is necessary to disrupt (lysis) the membrane structure of a cell to thereby cause the content of the cell to be extracted outside the cell. A microbe is generally defined as a living organism that is microscopic, or smaller in size, such as a bacterium, archaebacterium, protist, fungus, and so forth. The microbes differ in feature from each other, and bacteria fall into two broad categories, that is, gram-negative bacteria, such as *Escherichia coli* (*E. coli*), and so forth, and gram-positive bacteria, such as *Bacillus subtilis* (*B. subtilis*), and so forth, on the basis of a difference in the membrane structure of a cell. For example, a cell wall of a gram-positive bacterium has a peptidoglycan layer greater in thickness, and higher in density than that of a cell wall of a gram-negative bacterium. Further, in the case of a fungus such as *Candida albicans* (*C. albicans*), and so forth, major constituents of a cell wall thereof is β-glucan, and chitin, and the fungus differs in composition from the bacteria described as above. Accordingly, in the case of making use of enzymatic or chemical method for cell lysis, different protocol is needed for each type of targeted cell. In the case of using an enzyme, in particular, zymolyase is commonly used for fungus in contrast to lysozyme that is commonly used for bacteria. Further, lysostaphin is commonly used for lysis of cell wall of *Staphylococcus aureus* (*S. aureus*) among the gram-positive bacteria because lysostaphin is effective in use.

RELATED ART LITERATURE

Patent Documents

Patent Document 1

Japanese Patent No. 3866762

Patent Document 2

Japanese Examined Patent Application Publication No. Hei7 (1995)-002120

The enzymatic or chemical method for cell lysis has been widely adopted in a commercially available nucleic-acid extraction kit. However, many nucleic-acid extraction kits require a lot of time and most of the treatment time is engaged by the lysis process. Further, this lysis treatment includes a plurality of process steps such as steps for addition of a reagent, stirring, and so forth, respectively, and is therefore complicated. Accordingly, in the cases where rapid detection is required, including the case of infectious disease control, the case of safe guards against bio-terrorism, and so forth, there is a demand for shortening of the treatment time for the cell lysis, in particular.

Furthermore, as described above, a uniform protocol is not applicable to the enzymatic or chemical method for cell lysis, and there is the need for varying an enzyme, and a protocol according to the type of a cell, which renders the method complicated. In the case of testing a specimen containing an unknown microbe, in particular, it is necessary to conduct tests by use of a plurality of protocols. Further, long-chain nucleic acid can be obtained in this case, however, as enzyme reaction time is long, the method is therefore lacking in rapidity. For this reason, the enzymatic or chemical method for cell lysis is not suited to an application requiring rapidity.

SUMMARY OF THE INVENTION

Exemplary embodiments of the present invention address the above disadvantages and other disadvantages not described above. However, the present invention is not required to overcome the disadvantages described above, and thus, an exemplary embodiment of the present invention may not overcome any disadvantages.

It is one of illustrative aspects of the present invention to provide a nucleic acid extraction method applicable to microbes in a relatively wide range, and capable of rapidly extracting nucleic acid.

According to one or more illustrative aspects of the invention, there is provided a nucleic acid extraction method for extracting nucleic acid from a cell, said method comprising the steps of introducing a cell suspension into a vessel, sealing the vessel, and heating the cell suspension housed in the vessel up to a prescribed highest temperature at not lower than 100° C. with the vessel held in a sealed state.

BRIEF DESCRIPTION OF THE DRAWINGS

FIG. 6 is a view showing comparison of effects of DNA extraction by respective treatments applied to *C. albicans* with each other; and FIG. 7 is a view showing effects of DNA extraction by application of high-temperature heating-treatments to *C. albicans* in various cell lysis accelerators (surfactants).

DETAILED DESCRIPTION OF EXEMPLARY EMBODIMENTS

Embodiments of a nucleic acid extraction method according to the invention are described hereinafter.

Embodiment 1

There is described hereinafter an experiment conducted for finding a relationship between a condition under which a cell suspension is heated up, and variation in the temperature of a cell suspension, which represents Embodiment 1 of the invention.

Use can be made of a boil-lock type tube (capacity: 0.6 ml) having a mechanical structure for sealing purposes to serve as a vessel for housing the cell suspension therein. Further, for a heating means, use can be made of an oil bath (temperature range: from room temperature to 200° C.). Furthermore, an apparatus for use in carrying out this experiment, and the present invention is not limited thereto.

There are described hereinafter the steps of a procedure for the experiment:

In the step 1, in conjunction with setting of a thermocouple in the vessel, a cell suspension, together with 20 μl of an introduction buffer [20 mM Tris-HCl {tris (hydroxymethyl) aminomethane hydrochloride}, and 2% TritonX-100], was introduced into the vessel so as not to include a gas space therein. Further, the vessel was sealed by making use of a mechanical structure. Herein, the introduction buffer is used for higher efficiency as well as stabilization in extraction of nucleic acid, and Tris-HCl is a buffer solution for inhibiting variation in pH value of the solution, and stably holding nucleic acid as extracted. Further, TritonX-100 is a polymer produced by SIGMA Corp., having a composition of $\{C_{14}H_{220}(C_2H_{40})n\}$, the polymer being a surfactant to be added as a cell lysis accelerator.

In the step 2, the heating means was preheated up to a set temperature.

In the step 3, the vessel was kept in contact with a heater (for example, oil in the oil bath) of the heating means for 30 seconds to be thereby heated.

In the step 4, the vessel was detached from the heater of the heating means.

In the step 5, measurement was made on variation in the temperature of the cell suspension, during heating, and after the heating, respectively, by use of a data logger connected to the thermocouple.

Figure 1:
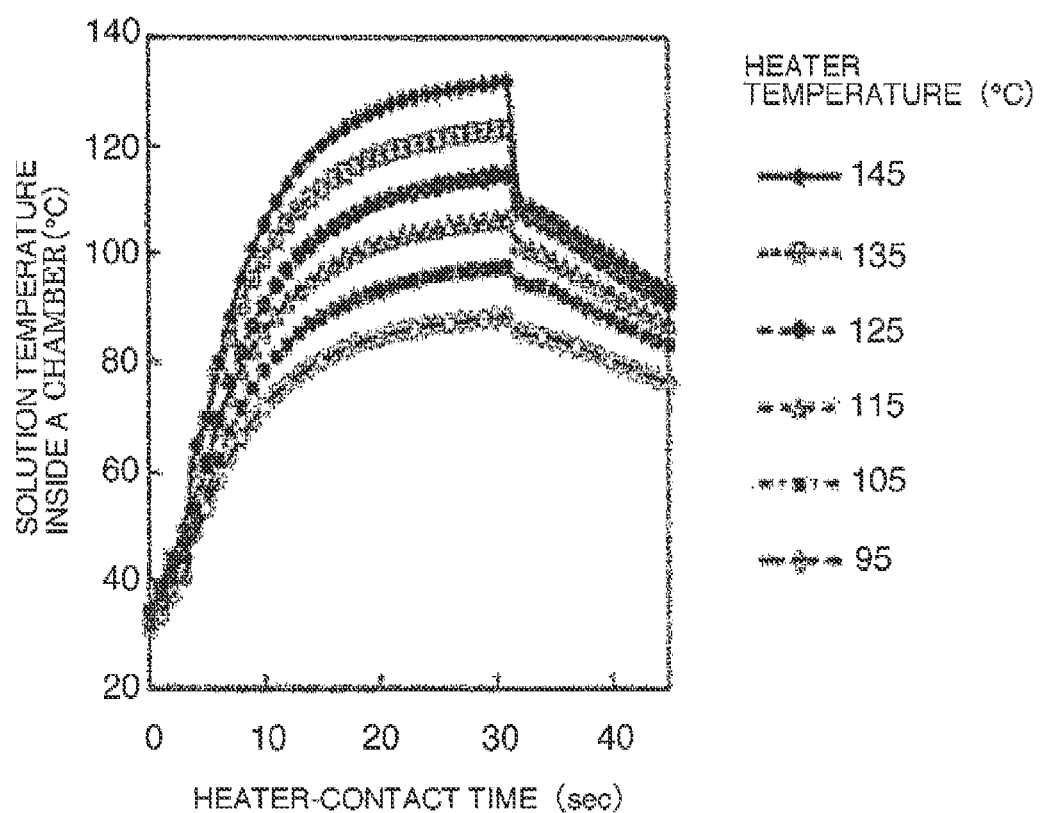
FIG. 1 is view showing a relationship between time during which a vessel was in contact with a heater of a heating means which preheated to a set value, and the temperature of a solution in the vessel, measured by use of a data logger.

FIG. 1 is a view showing the variation in the temperature, measured by repeating the procedure described as above at the various set value.

With a graph shown in FIG. 1, the horizontal axis indicates time during which the vessel was in contact with the heater of the heating means while the vertical axis indicates the temperature measured by use of the data logger. Further, a measurement was made on the temperature of the cell suspension in each case where the temperature of the heater was set to 95° C., 105° C., 115° C., 125° C., 135° C., and 145° C., respectively.

As shown in FIG. 1, it was possible to rapidly heat up the cell suspension up to 100° C. or higher by increasing the temperature of the heater to around 115° C. or higher. Further, as shown in FIG. 1, a rapid decrease in temperature, due to detachment of the vessel from the heater, was observed as shown in the form of variation in temperature after the elapse of 30 seconds from the start of heating.

Embodiment 2

Next, there is described hereinafter a relationship between the highest treatment temperature in the course of DNA extraction from *E. coli*, and extractability, which represents Embodiment 2 of the invention.

There are described hereinafter the steps of a procedure for an experiment conducted to acquire results of DNA extraction from *E. coli*:

In the step 1, *E. coli* DH-5α strain was cultured in an LB medium overnight.

In the step 2, a culture solution of *E. coli*, and the introduction buffer in two-fold concentrations (40 mM Tris-HCl, and 4% of TritonX-100), in equal proportions, were mixed with each other to prepare a sample.

In the step 3, 20 μl of the sample was introduced into the vessel, and the vessel was subsequently sealed.

In the step 4, the vessel was brought into contact with a heater of a heating means as preheated, thereby heating the vessel for 30 seconds.

In the step 5, the vessel was detached from the heater.

In the step 6, the sample after heated was taken out of the vessel to be transferred to a test tube.

In the step 7, the test tube with the sample introduced therein was centrifuged at $15300 \times g$ for 10 minutes.

In the step 8, a supernatant liquid was transferred to a new test tube in order to prevent the sample from absorbing yet-to-be-crushed bacteria, as precipitated, and residues.

In the step 9, real-time PCR was carried out with the use of a primer capable of amplifying gyrB gene that is present in an *E. coli* genomic DNA. The samples identical to each other were evaluated with the use of four types (64, 180, 409, and 896, in bp) of primer sets differing in amplification length from each other.

In the step 10, the experiment was repeatedly conducted three times to find a mean value, and the standard deviation.

In the step 11, the treatment temperature at the time of heating after 30 seconds, obtainable on the basis of results of the experiment according to Embodiment 1, and the preheated temperature of the heating means, are plotted along the horizontal axis while an extracted amount (a detection value) of DNA in the sample, PCR being applicable thereto, as worked out by real-time PCR, was plotted along the vertical axis. For error bars, use is made of the standard deviation.

Figure 2:
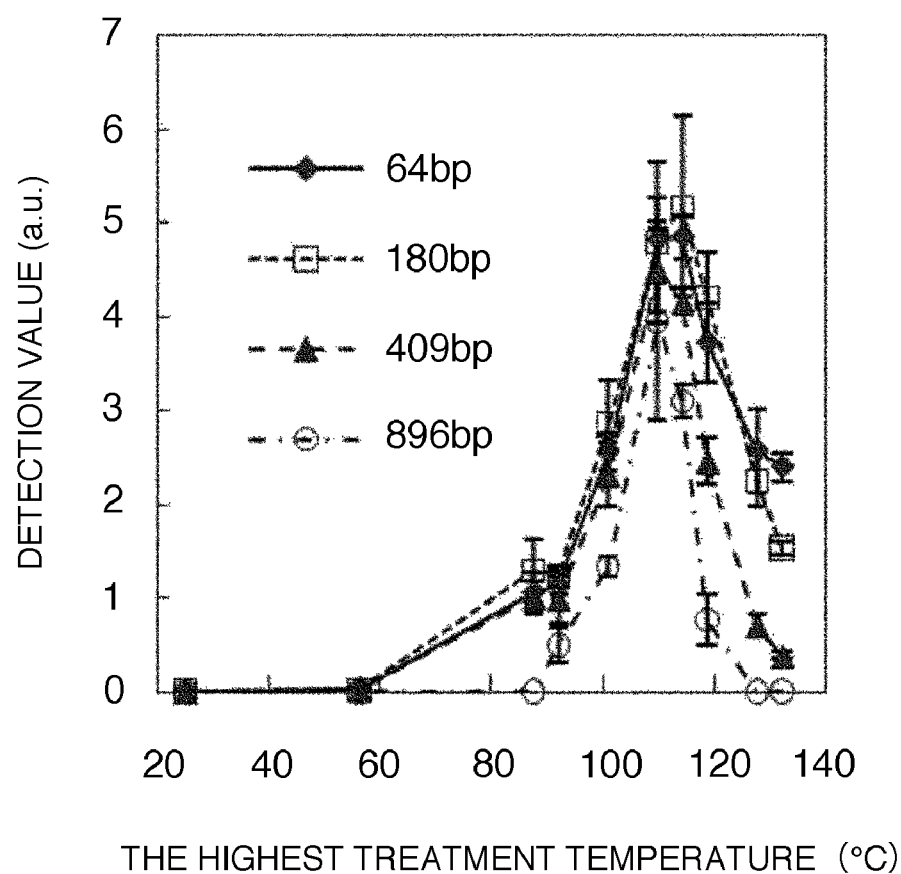
FIG. 2 is view showing a relationship between the highest treatment temperature at the time of heating applied to *E. coli*, and a detection value of each length of extracted DNA.

FIG. 2 is a view showing a plot obtained in the step 11, described as above.

As shown in FIG. 2, the detection value increased due to application of a heating-treatment whereby the highest treatment temperature reached 100° C. or higher, and the detection value reached the maximum value when the highest treatment temperature was at about 115° C. At a temperature in excess of about 115° C., the detection value decreased. The reason for this is presumably because if a treatment temperature is excessively high, progress is made in fragmentation of DNA, and parts of the DNA, have come to fail functioning as a template for PCR amplification. As shown in FIG. 2, a substantially equivalent tendency was shown in the case of evaluation being made with the use of any primer set among the four types (64, 180, 409, and 896, in bp, respectively) of the primer sets, whatever amplification length may be, and a high detection value was obtained at the highest treatment temperature in a range of about 105° C. to 125° C.

Embodiment 3

Next, there is described hereinafter a relationship between heating-treatment time in the course of DNA extraction from *E. coli*, and extractability, which represents Embodiment 3 of the invention.

There are described hereinafter the steps of a procedure for an experiment:

In the step 1, a sample was prepared as is the case with Embodiment 2.

In the step 2, a heating means was preheated at 125° C., which is a condition equivalent to the condition under which the extracted amount of DNA was found at the maximum value upon heating the vessel for 30 seconds in the case of the experiment shown in Embodiment 2.

In the step 3, the vessel was brought into contact with a heater of the heating means, thereby heating the vessel for given time (for a duration in a range of 0 to 300 seconds).

In the step 4, the vessel was detached from the heater, and the sample was introduced into a new test tube.

In the step 5, the test tube with the sample introduced therein was centrifuged at 15300$^{\times g}$ for 10 minutes.

In the step 6, a supernatant liquid was transferred to the new test tube in order to prevent the sample from absorbing yet-to-be-crushed bacteria, as precipitated, and residues.

In the step 7, RT-PCR was carried out with the use of a primer capable of amplifying gyrB gene that is present in an E. coli genomic DNA. Samples identical to each other were evaluated with the use of a primer set having an amplification length 180 bp.

Figure 3:
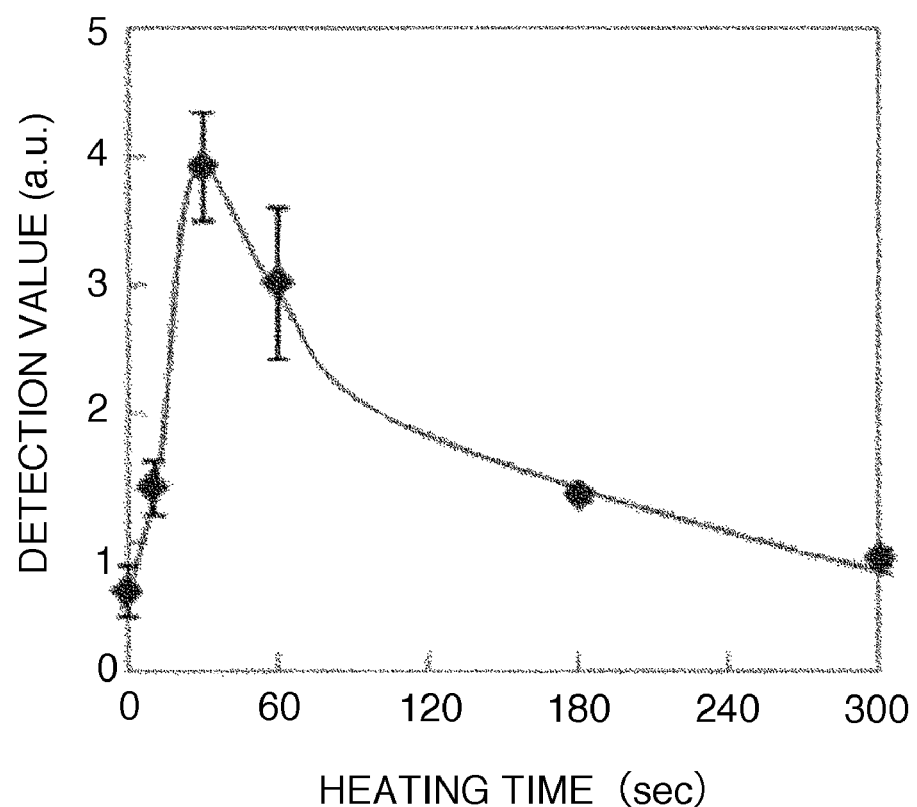
FIG. 3 is a view showing a relationship between heating time for *E. coli*, and a detection value of extracted DNA.

FIG. 3 is a view showing a relationship between heating time in the step 3, and a DNA amount (a detection value) obtained in the step 7, in which the horizontal axis indicates the heating time while the vertical axis indicates the detection value.

As shown in FIG. 3, it was confirmed that a genomic DNA to which PCR amplification is applicable was extracted with high efficiency by a treatment applied for about 30 seconds. However, progress was made in decomposition of the DNA due to the heating-treatment applied over long time, thereby rendering the PCR amplification harder to perform. As is evident from FIG. 3, the heating time around 30 seconds is most preferable, however, if [the detection value=2] is assumed as a threshold value, the treatment for at least 15 seconds, and less than 120 seconds is considered preferable.

Embodiment 4

Next, there is described hereinafter an experiment for DNA extraction from C. albicans, which represents Embodiment 4 of the invention.

A procedure for the experiment comprises the following steps:

In the step 1, C. albicans was cultured in a GP medium for a period of 15 hours;

In the step 2, a culture solution of C. albicans, and the introduction buffer in two-fold concentrations (40 mM Tris-HCl, and 4% of TritonX-100), in equal proportions, were mixed with each other to thereby prepare a sample;

In the step 3, 20 μl of the sample was introduced into the vessel;

In the step 4, the vessel was brought into contact with a heater of a heating means as preheated, thereby heating the vessel for 30 seconds;

In the step 5, the vessel was detached from the heater;

In the step 6, the sample after heated was taken out of the vessel to be transferred to a test tube;

In the step 7, the test tube with the sample introduced therein was centrifuged at 2000$^{\times g}$ for 3 minutes;

In the step 8, a supernatant liquid was transferred to a new test tube in order to prevent the sample from absorbing yet-to-be-crushed cell, as precipitated, and residues.

In the step 9, real-time PCR was carried out with the use of a primer capable of amplifying 112 bp of TOP2 gene present in a C. albicans genomic DNA.

In the step 10, a sterilization treatment (heating at 80° C. for 20 minutes), and an autoclave sterilization treatment (heating at 121° C. for 15 minutes) were applied to the sample, and the sample was also centrifuged before real-time PCR measurement was made on the supernatant liquid.

The sterilization treatment was set on the basis of [Rapid simultaneous detection and identification of six species Candida using polymerase chain reaction and reverse line hybridization assay] {J. Microbiol. Methods. 2007 May; 69 (2): 282-7.}

Figure 4:
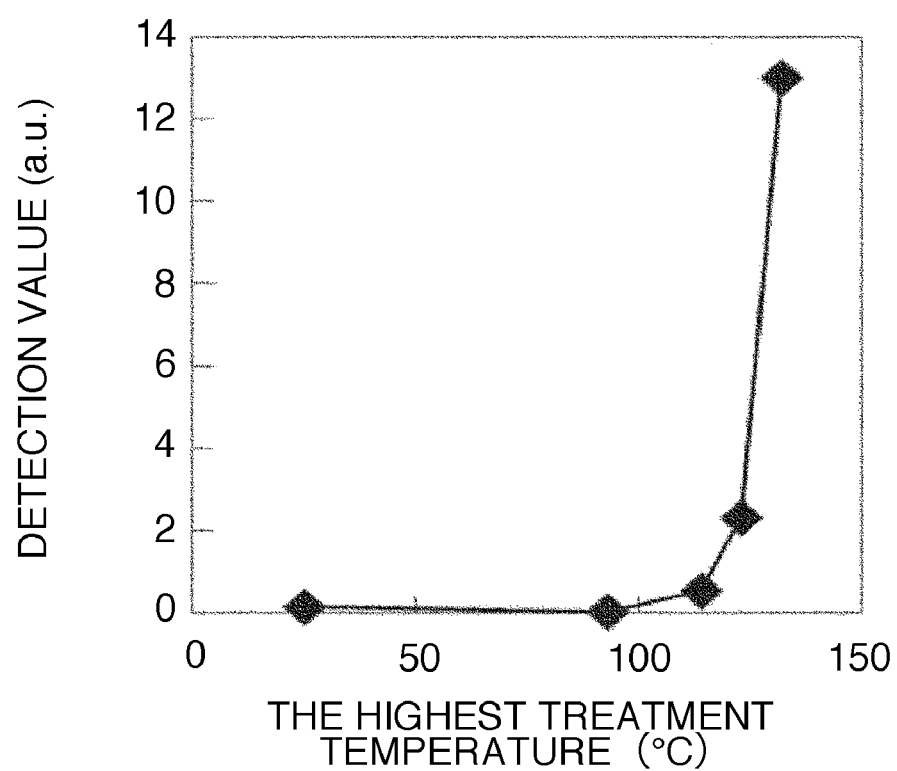
FIG. 4 is a view showing a relationship between the highest treatment temperature at the time of heating applied to *C. albicans*, and a detection value of extracted DNA.

FIG. 4 is a view obtained by plotting the highest treatment temperature at the time of heating, grasped on the basis of results of the experiment according to Embodiment 1, and a preheating temperature of the heating means, on the horizontal axis, and by plotting a PCR adaptable DNA amount (a detection value) extracted in the sample, as worked out from real-time PCR, on the vertical axis. For error bars, use is made of the standard deviation.

As shown in FIG. 4, an increase in the DNA amount as extracted was observed at the highest treatment temperature in a range not lower than 100° C., and the DNA amount was extracted with high efficiency at not lower than 130° C. DNA was not detected out of the sample to which the sterilization treatment, and the autoclave treatment were applied.

Embodiment 5

Next, there is described hereinafter an experiment conducted for comparing the case of DNA extraction by use of the present invention with the case of the sterilization treatment, which represents Embodiment 5 of the invention.

As shown in FIG. 4, with Embodiment 4 described as above, DNA was not extracted at 95° C., and DNA was extracted with high efficiency at the time of the treatment at 132° C. The sterilization treatment is well known as a treatment similar to the DNA extraction according to the present invention. As a condition for sterilization, a condition of, for example, heating at 80° C. for a time period of 20 minutes, and so forth have since been in use. However, it is not that DNA extraction is enabled by simply meeting this sterilization condition. In order to demonstrate this, the following experiment was conducted. In the experiment, an observation using an optical microscope was made on C. albicans species after respective treatments for staining by use of ethidium homodimer as a fluorescent reagent capable of staining a dead cell without staining a live cell, the C. albicans being placed in a bright field, and under irradiation with an excitation light, respectively, thereby having compared photographed images with each other.

Figure 5:
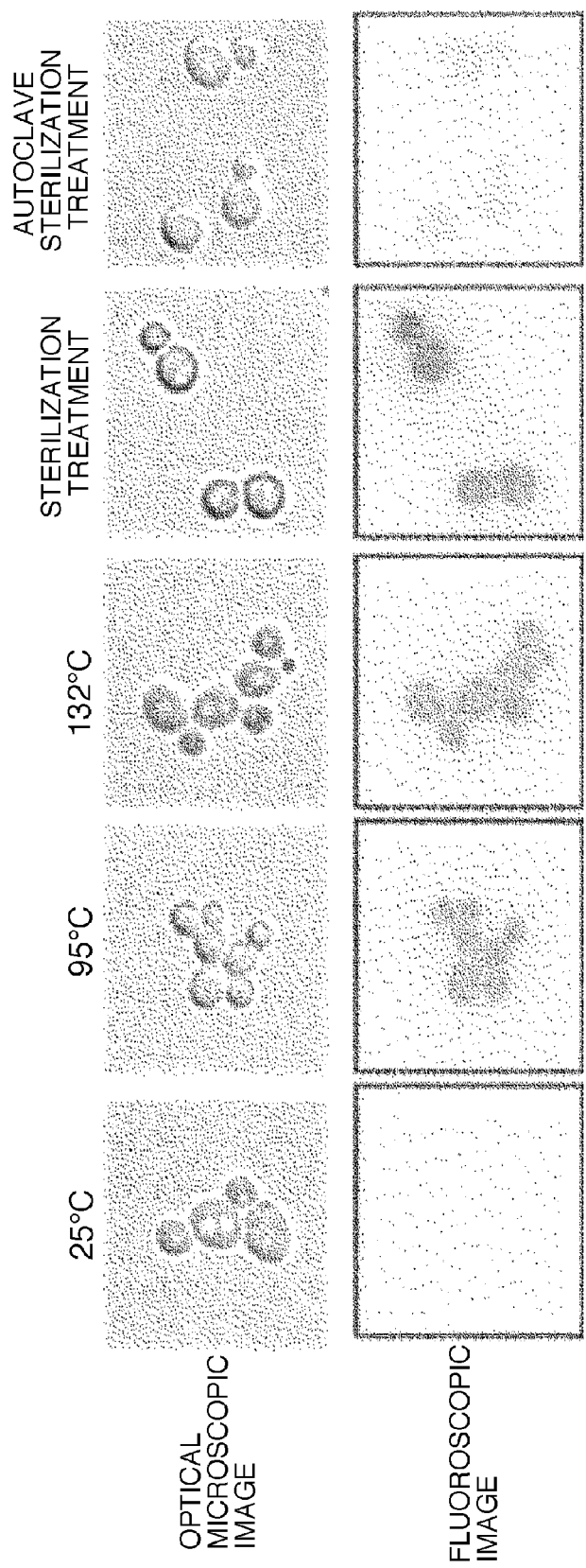
FIG. 5 is a view showing images of *C. albicans* cells obtained after application of various heating treatment differing in heating condition from each other.

FIG. 5 is a view showing optical microscopic images, and fluoroscopic images, obtained after application of the treatments (the highest treatment temperature: 25° C., 95° C., and 132° C., respectively), the sterilization treatment, and the autoclave sterilization treatment, applied in Embodiment 4, respectively. Further, FIG. 6 is a view showing comparison of effects of DNA extraction by the respective treatments with each other.

As shown in FIG. 5, fluorescence was not detected by the treatment at 25° C., applied in Embodiment 4, thereby confirming that C. albicans was not dead. On the other hand, fluorescence was observed at 95° C., thereby confirming that sterilization was effected. Similarly, fluorescence was also confirmed at 133° C.

Further, as shown in FIG. 6, a detection value equivalent to the detection value of the sample without heating applied thereto (for example, the treatment at 25° C., applied in Embodiment 4) was exhibited from the samples after the sterilization treatment, and the autoclave sterilization treatment, respectively, thereby confirming that DNA was hardly detected. Thus, it was demonstrated that DNA was not necessarily detected even under conditions suitable for sterilization.

Embodiment 6

Next, there is described hereinafter enhancement in extraction efficiency, achieved by joint use of a surfactant SDS (sodium dodecyl sulfate) as a cell lysis accelerator, which represents Embodiment 6 of the invention.

FIG. 7 is a view showing DNA extraction effects of high-temperature heating-treatments applied to *C. albicans* in various cell lysis accelerators (surfactants). In the figure, the DNA extraction effect in the case of using TritonX-100 as a cell lysis accelerator to be added to a sample before the heating is compared with that in the case of using SDS as the cell lysis accelerator.

As shown in FIG. 7, it was possible to extract DNA from *C. albicans* with higher efficiency in the case of using SDS as the cell lysis accelerator than in the case of using TritonX-100. In FIG. 7, in the case of the high-temperature heating-treatment at, for example, 132° C. of the highest treatment temperature, the detection value is found at 300 or more if SDS is added.

It is evident from this that the cell lysis accelerator is selectable according to usage of DNA that is extracted. It need only be sufficient to use SDS, for example, in the case where highly sensitive detection of DNA is required whereas, in the case of using DNA in an enzyme reaction that is interfered with by SDS, it need only be sufficient to use TritonX-100, that is, a surfactant milder than SDS.

Further, it can be considered that optimal conditions for the DNA extraction, such as treatment temperature and treatment time, will vary according to strength of a dissolving power of the cell lysis accelerator. There is a possibility that in the case of using a powerful cell lysis accelerator such as SDS, sufficient disruption occurs to the membrane structure of a cell at a treatment-temperature lower than the treatment-temperature in the case of using a milder surfactant such as TritonX-100, thereby enabling DNA to be extracted.

Next, there are described hereinafter a variation of the present invention, and an application example thereof.

(Temperature Reduction after the High-Temperature Treatment)

The following step can be selected as a step for temperature-reduction after the high-temperature treatment:

(A-1) rapid cooling with the vessel held in a sealed state;

If a sample after heated, together with the vessel, is subjected to rapid cooling by use of a Peltier element while the vessel is held in a sealed state, this will cause occurrence of a thermal shock, thereby enhancing a cell-disruption efficiency, so that a nucleic acid extraction rate is enhanced. This is an effective method for a cell having a hard structure such as gram-positive bacteria, fungus, and so forth.

(A-2) natural cooling with the vessel held in a sealed state;

In the case of natural cooling of a sample subsequent to heating with the vessel held in the sealed state, a thermal shock is prevented from acting on the sample, so that nucleic acid in such a state as to inhibit damaging thereof can be extracted. This method enables extraction of a long-chain nucleic acid, and is therefore effective when a long PCR amplification product is required.

(Release from the Sealed State)

As timing for releasing the vessel from the sealed state, the following timing can be selected:

(B-1) release execution with the vessel in a high-temperature held state at not lower than 100° C.;

If the vessel is released from the sealed state during a time period when the vessel subsequent to heated is at a high temperature not lower than 100° C., an internal pressure of the vessel at the time of a release is not lower than atmospheric pressure, so that there occurs a rapid change in pressure. For this reason, a shearing force is caused to occur, thereby enhancing cell disruption efficiency, leading to enhancement in a nucleic acid extraction efficiency. This is an effective method for the cell having the hard structure such as the gram-positive bacteria, fungi, and so forth.

(B-2) release execution after the vessel is cooled to a temperature not higher than 100° C., and the internal pressure is reduced down to the atmospheric pressure;

If the vessel is released from the sealed state after the vessel subsequent to heating is cooled down to 100° C. or lower, this will prevent a shearing force from acting at the time of the release, so that nucleic acid in such a state as to inhibit damaging thereof can be extracted. This method enables extraction of a long-chain nucleic acid, and is therefore effective when a long PCR amplification product is required.

(Joint Use of a Cell Lysis Accelerator)

Use of a cell lysis accelerator enables efficient extraction of nucleic acid against the cell having the hard structure, such as the gram-positive bacteria, fungi, and so forth, and a cell in a more solid state, such as a spore, oocyst, and so forth. Timing for adding the cell lysis accelerator, includes the following:

(C-1) addition before the high-temperature treatment;

In the case of adding a cell lysis accelerator to a sample before the high-temperature treatment, the membrane structure of a cell is weakened by the agency of the cell lysis accelerator to thereby cause the high-temperature treatment to effectively act on the sample, so that nucleic-acid extraction efficiency is enhanced. By virtue of the high-temperature treatment applied in the cell lysis accelerator, the action of the high-temperature treatment can be effectively exhibited. This method is effective in the case where a sample quantity is small, and therefore, nucleic acid need be extracted under a single condition with greater certainty.

(C-2) addition after the high-temperature treatment:

In the case of adding a cell lysis accelerator to a sample after the high-temperature treatment, it is possible to cause the cell lysis accelerator to effectively act on the sample after the membrane structure of a cell is weakened by virtue of the high-temperature treatment, so that nucleic acid can be extracted with high efficiency in a short time. This method is effective for a cell having a solid structure The cell lysis accelerator can include alkali (NaOH, KOH, etc.), acid (HCl, $H_2SO_4$, etc.), enzyme (proteinase K etc, polysaccharide-degrading enzyme: chitinase, lysozyme, zymolyase etc.) a surfactant (anionic: SDS, etc., cationic: CTAB (cetyltrimethylammonium bromide), etc., nonionic: Triton-X, etc., amphipathic: betaine (generic term for compounds having a specific structure, including trimethylglycin, etc.), an oxidation-reduction agent (solution of hydrogen peroxide, β-mercaptoethanol, dithiothreitol, etc.), an protein denaturant (guanidine hydrochloride, urea, etc.), and a chelating agent {ETDA (ethylenediamine tetraacetic acid), etc.}. A plurality of the cell lysis accelerators described as above may be mixed with each other to be put to use. A buffer solution may be added thereto as necessary.

(High-Temperature Treatment Applied a Plurality of Times)

High-temperature heating (heating up to 100° C. or higher) and cooling may be repeatedly applied a plurality of times. This method is effective for the cell having the hard structure, in particular, such as the gram-positive bacteria, fungi, and so forth. Specific steps of the method include the following:

(D-1); the cooling step (A-1) described as above can be performed after the high-temperature treatment, and subsequently, the high-temperature treatment can be performed again. Both heating and cooling are executed at least twice.

(D-2); the cooling step (A-2) described as above can be performed after the high-temperature treatment, and subsequently, the high-temperature treatment can be performed again. In this case as well, both heating and cooling are executed at least twice.

(D-3); a release step (B-1) can be performed after the high-temperature treatment, and subsequently, the high-temperature treatment can be performed again. In this case as well, both heating and cooling are executed at least twice.

(Reaction Vessel)

As the vessel (a reaction vessel) for use in heating, use can be made of, for example, the following:

(E-1) a plastic tube for reaction;
(E-2) a heat-sealable bag;
(E-3) a glass test tube;
(E-4) a micro TAS chip (Complete Filling Up of the Vessel with a Liquid)

Control of an internal state of the vessel can render it possible to speed up transition to a high-temperature pressurized state. The following specific methods are available:

(F-1); the cell suspension is introduced into the vessel in such a way as not to permit a bubble, a gas space, and so forth to be left out therein before the vessel is sealed. Subsequently, a transition to the step of heating is made in this method.

(F-2); a solvent having a high boiling point, such as a mineral oil, and so forth, is stratified in a gas space of a cell suspension small in quantity, in relation to the internal volume of the vessel. By so doing, airtightness can be enhanced. In this case as well, a transition to the step of heating is made after the vessel is sealed. In this case, heating at the boiling point of the solvent, or higher is applied after a gas phase part is filled up with vapor, having reached a saturated vapor pressure. For this reason, the vessel can be more rapidly pressurized to thereby reach a high temperature at 100° C. or higher.

(Mechanical Sealing of the Vessel)

If the vessel is mechanically sealed, this will enable the sealed state of the vessel to be prevented from being cancelled at the time of a rise in the internal pressure of the vessel. By so doing, the heating-treatment can be stably applied.

(G-1); as an example of mechanical sealing, there is available a method for pressing down (permanently-setting) the vessel with a member in a shape pairing off with the vessel.

(Favorable Conditions for Gram-Negative Bacteria)

(H-1); as an example of a favorable heating condition for gram-negative bacteria, there can be cited a condition under which heating time is not less than 15 seconds, and less than 2 minutes while the highest treatment temperature is in a range of 105° C. to 125° C. (refer to FIG. 2).

(Favorable Conditions for Gram-Positive Bacteria, and Fungi)

(I-1); as an example of a favorable heating condition for gram-positive bacteria, and fungi, there can be cited a condition under which heating time is less than one minute, and the highest treatment temperature is in a range of 125° C. to 160° C. (refer to FIG. 4). (provided that TritonX-100 is added as the cell lysis accelerator)

(Preferable Capacity for Uniform Heating in a Short Time)

As a preferable capacity of the vessel, capable of uniformly heating a sample in a short time during the step of heating, there can be cited the following ranges:

(J-1); not more than 2 ml at the most;
(J-2); preferably not more than 0.6 ml; and
(J-3); more preferably not more than 0.2 ml (Target Cell)

A cell as the target for the nucleic acid extraction method according to the present invention is primarily a microbial cell.

A microbe can be selected from the group of species, consisting of *Acinetobacter* species, *Actinomyces* species, *Aerococcus* species, *Aeromonas* species, *Alcaligenes* species, *Bacillus* species, *Bacteroides* species, *Bordetella* species, *Branhamella* species, *Brevibacterium* species, *Campylobacter* species, *Candida* species, *Capnocytophaga* species, *Chromobacterium* species, *Clostridium* species, *Corynebacterium* species, *Cryptococcus* species, *Deinococcus* species, *Enterococcus* species, *Erysipelothrix* species, *Escherichia* species, *Flavobacterium* species, *Gemella* species, *Haemophilus* species, *Klebsiella* species, *Lactobacillus* species, *Lactococcus* species, *Legionella* species, *Leuconostoc* species, *Listeria* species, *Micrococcus* species, *Mycobacterium* species, *Neisseria* species, *Cryptosporidium* species, *Nocardia* species, *Oerskovia* species, *Paracoccus* species, *Pediococcus* species, *Peptostreptococcus* species, *Propionibacterium* species, *Proteus* species, *Pseudomonas* species, *Rahnella* species, *Rhodococcus* species, *Rhodospirillum* species, *Staphylococcus* species, *Streptomyces* species, *Streptococcus* species, *Vibrio* species, and *Yersinia* species. The present invention is applicable to not only microbes, but also animal cells, insect cells, plant cells, mycoplasmas, viruses, and so forth. A plurality of the cells described as above, differing in species from each other, may mixedly present in the target for the treatment according to the present invention. Further, there exists a microbe that takes such a form as an endospore, and a spore when it is in a poor nutritional state, however, the present invention is applicable to a microbe in whatever state a cell thereof may be owing to such a growing condition as described.

(Type of Nucleic Acid)

Nucleic acid as the target for the nucleic acid extraction method according to the present invention is primarily a genomic DNA, ribosomal RNA, and plasmid DNA.

(Application)

The nucleic acid extraction method according to the present invention can be applied to a raw extraction liquid (for a silica-membrane method, a method using charged particle, a phenol/chloroform method, etc.) of nucleic acid purification, a template for nucleic acid amplification (PCR, RT-PCR, LAMP, NASBA, etc.), an intended target for nucleic acid detection (real-time PCR detection, microarray detection, hybridization protection assay, nucleic acid sequencing, etc.), and so forth.

Further, the nucleic acid extraction method according to the present invention can also be applied to a nucleic acid purification kit. There can be cited, for example, a kit making use of a silica-membrane, a charged magnetic particle, and so forth, as a carrier, or one making use of an alcohol precipitation method.

As described in the foregoing, with the nucleic acid extraction method according to the invention, a nucleic acid can be rapidly extracted by heating the cell suspension up to the prescribed highest temperature at not lower than 100° C. with the vessel held in the sealed state.

With the nucleic acid extraction method according to the present invention, nucleic acid can be rapidly extracted by heating the cell suspension up to the prescribed highest temperature at not lower than 100° C. with the vessel held in the sealed state.

It is to be understood that an application range of the invention is not limited to Embodiments described in the foregoing. The invention is widely applicable to a nucleic acid extraction method for extracting nucleic acid from a cell.

While the present invention has been shown and described with reference to certain exemplary embodiments thereof, other implementations are within the scope of the claims. It will be understood by those skilled in the art that various changes in form and details may be made therein without departing from the spirit and scope of the invention as defined by the appended claims.

What is claimed is:

1. A nucleic acid extraction method for extracting nucleic acid from a cell, said method comprising the steps of:
introducing a cell suspension into a vessel,
blending a cell lysis accelerator with the cell suspension, sealing the vessel, and
heating the cell suspension housed in the vessel up to a prescribed highest temperature in a range of 125° C. to 160° C. with the vessel held in a sealed state,
wherein time for heating the vessel, during the step of heating the cell suspension, is less than 60 seconds,
wherein the cell is a fungus.

2. The nucleic acid extraction method according to claim 1, wherein time for heating the vessel, during the step of heating the cell suspension, is in a range of 15 to 40 seconds.

3. The nucleic acid extraction method according to claim 1, further comprising the step of cooling the cell suspension heated up to the prescribed highest temperature with the vessel kept in the sealed state.

4. The nucleic acid extraction method according to claim 1, further comprising the step of releasing the vessel already subjected to the step of heating from the sealed state while the vessel is in a state where an internal pressure thereof is at atmospheric pressure or higher.

5. The nucleic acid extraction method according to claim 1, further comprising the step of cooling the cell suspension heated up to the prescribed highest temperature before heating the cell suspension again.

6. The nucleic acid extraction method according to claim 1, wherein the vessel is sealed without a gas space included therein during the step of sealing the vessel.

7. The nucleic acid extraction method according to claim 1, wherein a solvent higher in boiling point than the cell suspension is enclosed in the vessel during the step of sealing the vessel.

8. The nucleic acid extraction method according to claim 1, wherein the step of heating the cell suspension comprises the step of preheating a heater up to a set temperature not lower than 100° C., and the step of bringing the vessel into contact with the heater heated up to the set temperature.

9. A nucleic acid extraction method for extracting nucleic acid from a cell, said method comprising the steps of:
introducing a cell suspension into a first vessel,
blending a cell lysis accelerator with the cell suspension,
sealing the first vessel, and heating the cell suspension housed in the first vessel up to a prescribed highest temperature in a range of 125° C. to 160° C. with the first vessel held in a sealed state,
centrifuging of the cell suspension in a range of 6 to 10 minutes, and
transfer of a resulting centrifuged supernatant liquid from the cell suspension to a second vessel in order to prevent the supernatant liquid from absorbing residue,
wherein the cell is a fungus.

10. The nucleic acid extraction method according to claim 9, wherein time for heating the vessel, during the step of heating the cell suspension, in a range of 15 to 40 seconds.

11. The nucleic acid extraction method according to claim 9, wherein a solvent is stratified in a gas space of the cell suspension in the vessel in order for the vessel to be sealed without a gas space.

12. The nucleic acid extraction method according to claim 9, wherein the heating is achieved by an oil bath.

13. The nucleic acid extraction method according to claim 1, wherein the vessel comprises of a boil-lock type tube.

* * * * *